(12) United States Patent
Marc et al.

(10) Patent No.: US 9,034,281 B2
(45) Date of Patent: May 19, 2015

(54) DEVICE FOR SEPARATING A MEMBRANE FROM A SUPPORT

(75) Inventors: Frederic Marc, Itterswiller (FR); Luc Felden, Colmar (FR); Gael Waiche, Molsheim (FR); Jean-Jacques Richert, Waldolwisheim (FR)

(73) Assignee: EMD Millipore Corporation, Billerica, MA (US)

( * ) Notice: Subject to any disclaimer, the term of this patent is extended or adjusted under 35 U.S.C. 154(b) by 262 days.

(21) Appl. No.: 13/579,996

(22) PCT Filed: Feb. 2, 2011

(86) PCT No.: PCT/IB2011/050457
§ 371 (c)(1),
(2), (4) Date: Aug. 20, 2012

(87) PCT Pub. No.: WO2011/104646
PCT Pub. Date: Sep. 1, 2011

(65) Prior Publication Data
US 2012/0315663 A1   Dec. 13, 2012

(30) Foreign Application Priority Data

Feb. 26, 2010   (FR) ...................................... 10 51422

(51) Int. Cl.
*B01L 9/00*    (2006.01)
*G01N 1/40*    (2006.01)

(52) U.S. Cl.
CPC .............. *B01L 9/52* (2013.01); *B01L 2200/026* (2013.01); *B01L 2300/0681* (2013.01); *B01L 2300/0822* (2013.01); *G01N 1/4077* (2013.01); *G01N 2001/4088* (2013.01)

(58) Field of Classification Search
CPC ................ B01L 9/52; B01L 2200/025; B01L 2300/0681
USPC ............................. 422/63, 67, 560, 563, 561
See application file for complete search history.

(56) References Cited

U.S. PATENT DOCUMENTS

| 6,864,097 | B1 | 3/2005 | Schembri et al. |
| 2004/0223890 | A1 | 11/2004 | Summers et al. |
| 2005/0036911 | A1 | 2/2005 | Sellers et al. |
| 2006/0239868 | A1 | 10/2006 | Sage et al. |

OTHER PUBLICATIONS

International Search Report and Written Opinion mailed May 11, 2011 in corresponding PCT application No. PCT/IB2011/050457.
International Preliminary Report on Patentability mailed Sep. 7, 2012 in corresponding PCT application No. PCT/IB2011/050457.

*Primary Examiner* — Jill Warden
*Assistant Examiner* — Dwayne K Handy
(74) *Attorney, Agent, or Firm* — Nields, Lemack & Frame, LLC

(57) ABSTRACT

A device (1, 100) for separating a membrane (81, 91) to analyze from a support (83, 93), the membrane being mounted in a frame (82, 92), itself mounted on a support, having a body (10) comprising a longitudinal recess (11, 110, 120) for translational reception of the assembly constituted by the frame mounted on the support, the recess having a first end (12) and a second end (13) and longitudinal sides (14A, 14B, 111, 121) facing each other between said two ends, the device having bearing means (30, 112, 122) for a first member of the frame/support group between the first and the second end of the recess, which are adapted to serve as a bearing for the first member of the frame/support group once the assembly is disposed in the recess, each of the sides having a ramp (15A, 15B, 112, 122) adapted to engage a gripping member (84, 73) of the second member of the frame/support group when the assembly is translationally moved from the first to the second end, said ramps being adapted to separate the support from the frame during said translational movement by bearing on said gripping member of the second member of the frame/support group, the first member of the frame/support group then bearing on the bearing means, such that the frame and the support are separated once the translational movement has arrived at the second end.

10 Claims, 4 Drawing Sheets

DEVICE FOR SEPARATING A MEMBRANE FROM A SUPPORT

The present invention generally relates to the field of the microbiological testing of liquids.

More particularly, the present invention concerns a method referred to as membrane filtration. This method consists of filtering a liquid sample on a porous membrane and then of depositing the membrane on a support containing, for example, solid or liquid growth media or a marking medium. The assembly is next incubated in order for the microorganisms of the sample retained on the membrane during filtration to be able to develop sufficiently to be visible to the naked eye. This simple method enables the microorganisms present in the sample to be counted and so to determine the degree of contamination thereof.

In certain microbiological analyses, it is necessary to separate the membrane from the support on which it has been deposited in order to continue the microbiological analysis, for example using an optical apparatus.

This is the context of the present invention. More particularly, in practice, the separation of the membrane and the support poses a certain number of problems. The membrane is fastened in a frame that is in general formed from a flexible elastic material. This frame is then mounted on a support containing a growth or marking medium to which the membrane adheres. Once the incubation has been carried out, to separate the membrane from the support, it is necessary to apply antagonistic traction forces by hand on the frame and on the support in order to separate them. The adhesive forces existing between the surface of the membrane and the content of the support resist that separation and it is difficult for an operator to obtain a uniform distribution of the traction forces on the surface of the membrane: this very often leads to a deterioration of the membrane by tearing, which makes it unusable to finish the analysis. Furthermore, as the incubation may take place up to temperatures of approximately 45° C. in the incubator, the frame of the membrane is softened on coming out of the incubator. This loss in stiffness of the frame makes a uniform distribution of the separating forces over the surface of the membrane even more difficult when attempting separation and increases the risk of deterioration of the membrane at this step.

The present invention aims to overcome these problems to enable the membrane to be separated easily from the support in reliable manner, without risking deterioration of the membrane.

To that end it provides a device for separating a membrane to analyze from a support, the membrane being mounted in a frame, itself mounted on a support, having a body comprising a longitudinal recess for translational reception of the assembly constituted by the frame mounted on the support, the recess having a first end and a second end and longitudinal sides facing each other between said two ends, the device having bearing means for a first member of the frame/support group between the first and the second end of the recess, which are adapted to serve as a bearing for the first member of the frame/support group once the assembly is disposed in the recess, each of the sides having a ramp adapted to engage a gripping member of the second member of the frame/support group when the assembly is translationally moved from the first to the second end, said ramps being adapted to separate the support from the frame during said translational movement by bearing on said gripping member of the second member of the frame/support group, the first member of the frame/support group then bearing on the bearing means, such that the frame and the support are separated once the translational movement has arrived at the second end.

Thus, advantageously, the present invention enables the membrane to be separated easily from the support in reliable manner by distributing the separating force uniformly by means of the adapted ramps. The reliability thus improves, and the risk of tearing the membrane is thereby strongly reduced.

According to an advantageous feature, the body has foot forming means adapted to form a space between the body and a surface on which the device is placed, the recess having, at least at its second end, a hole opening towards said space and the ramps have a profile adapted to guide the support towards said hole to eject the support from the device via the hole towards said space once the separation has been carried out and the translational movement has arrived at said second end.

Thus, advantageously, the support is directly ejected from the device while the frame carrying the membrane is itself directly accessible in the recess into which it was inserted beforehand. This advantageously avoids the unnecessary manipulations which could contaminate the membrane for the following part of the analyses.

According to an advantageous feature, the device further comprises a shuttle mounted for translational movement in the recess between said first and said second end, the shuttle having an opening adapted to accommodate the assembly during the translational movement and to serve as bearing means for the frame once the assembly has been placed in the opening between the first and the second end.

Thus, advantageously, the guidance in translational movement and the bearing for the frame are formed via a single part that is moveable relative to the body of the device which improves reliability and reduces the risk of deterioration of the membrane on separation.

According to an advantageous aspect of the invention, the shuttle has clamping means actuated by a cam action cooperating with the body of the device and which are adapted to clamp the frame once the shuttle has left the first end.

Thus, advantageously, the clamping means contribute to stiffening the frame during the separation operation, which enables better distribution of the separating forces over the surface of the membrane and contributes to limiting the risk of deterioration thereof at the time of the separation operation.

According to an advantageous feature, the device further comprises an ejecting lever rotatably mounted relative to the body in said space, and which is adapted to be pivoted by cam action on movement of the shuttle from the first to the second end so as to make the support come out of said space once the ejection has been performed via the hole.

Thus, advantageously, the support is made accessible to an operator without the operator having to move or raise the device, which appreciably improves the convenience of the separation operation.

According to other advantageous features, which may be combined:
  the device further comprises an adaptor provided for engaging with a flat provided on the support and for forming gripping means for the separation ramps.
  the device has fastening means for the adaptor provided for retaining the adaptor in a position in which the support is assembled with the adaptor before the frame-and-support assembly is placed in the recess.

Thus, advantageously, all types of support may be used with the device and a corresponding adaptor, and the putting in place of that adaptor may be carried out directly on the device which makes it possible to assemble and remove the supports from the adaptor with ease.

According to an advantageous feature, the device comprises a plurality of recesses provided with corresponding ramps, which recesses are each adapted to cooperate with a different predefined support-and-frame assembly.

According to another aspect, the present invention concerns a method of separating a membrane to analyze from a support, the membrane being mounted in a frame, itself mounted on a support using a device as described above, comprising the steps of:
- placing the assembly constituted by the frame and the support in the recess at its first end,
- causing the assembly to move translationally from the first to the second end of the recess to separate the support from the frame,
- removing the separated frame from the device.

According to another aspect, the invention concerns a method of separating a membrane to analyze from a support, the membrane being mounted in a frame, itself mounted on a support using a device as described above and comprising the steps of:
- assembling the support with the adaptor,
- placing the assembly constituted by the frame and the support with the adaptor in the recess at its first end,
- causing the assembly to move translationally from the first to the second end of the recess to separate the support from the frame,
- removing the separated frame from the device,
- removing the support from the adaptor.

The invention will be better understood on reading the description of an embodiment of a device and of the implementation of a method according to the invention, with reference to the accompanying drawings, given by way of non-limiting example, and in which.

Figure 1:
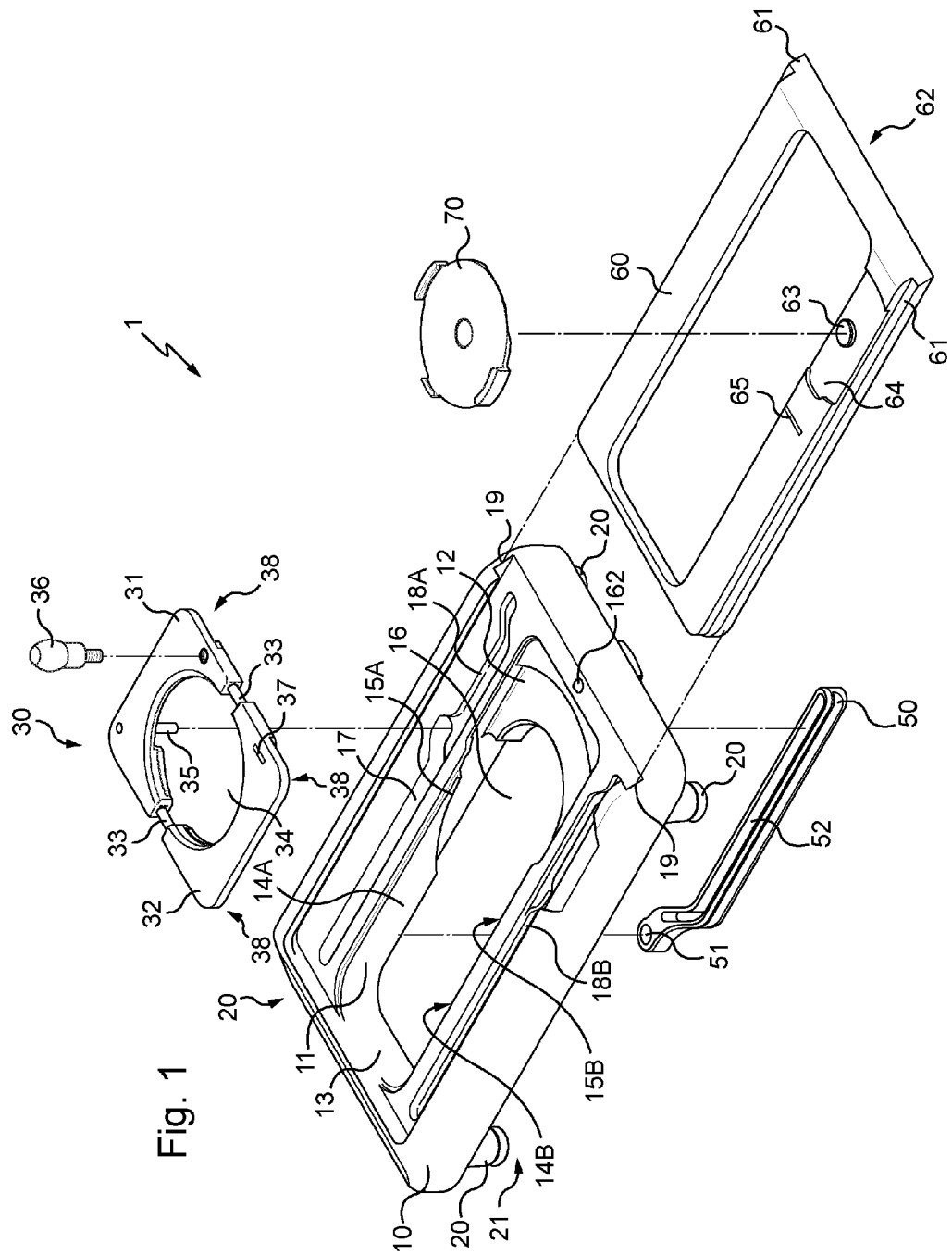
FIG. 1 is an exploded perspective view of a first embodiment of a device according to the invention.

As can be seen in FIG. 1, a separating device according to the invention comprises a body 10 which has a longitudinal recess 11, the recess having a first end 12 and a second end 13. The recess 11 further comprises two longitudinal sides 14A and 14B facing each other between said two ends 12 and 13. Each of the sides 14A, 14B respectively comprises a ramp 15A and 15B which are symmetrical and provided for separating the membrane from the support.

The body further comprises four feet 20 adapted to support the body above a surface on which the body is placed, so as to form a space 21 between the body and that surface.

The recess 11 comprises a hole 16 in its median portion extending to the second end 13.

The device further comprises a shuttle 30 mounted for translational movement above the recess 11 between its first end 12 and its second end 13. The shuttle 30 is formed with two halves 31 and 32 mounted for translational movement relative to each other along rods 33. Each of the halves 31, 32 is substantially U-shaped, and the two halves are assembled so as to form a shuttle together which has an opening 34.

The half 31 of the shuttle 30 further comprises a handle 36 adapted to be screwed into a hole provided for that purpose in half 31. The latter comprises, at one corner, a fixed stud 35 projecting from a back face and adapted to cooperate with a groove 17, forming a cam track, produced for that purpose in the body 10.

The device 1 further comprises an ejection lever 50 comprising at a first end a pivot 51 adapted to rotationally engage with a stud not shown provided for that purpose on the lower face of the body 10. The ejection lever, in addition to the pivot 51, is pierced along its length by a groove 52 forming a cam track. The free end of the stud 35 of the shuttle 30 is adapted to cooperate with said groove 52 by passing through the groove 17 which is open at the bottom.

The groove 17 which is open at the bottom is continued by a blind groove 18A forming a cam track and which extends towards the first end 12 of the recess 11.

A groove 18B, which is blind over its entire length, reproduces in symmetrical manner the combined profiles of the grooves 17 and 18A forming cam tracks on the body 10, on the opposite side relative to the recess.

In addition to the stud 35, the shuttle comprises, at its three other corners, three nipples not shown and of which the locations are referenced 38, a first on half 31 and the two others on half 32. The nipples 38 respectively engage in the groove 18A for the first and in the groove 18B for the two others.

Once the shuttle 30 has been inserted onto the recess 11, the device is closed by means of a cover 60 adapted to slide in channels 19 of the body thanks to rails 61 provided for that purpose on two of its opposite sides. The cover 60 further comprises a stud 63 surrounded by a recess 64, both of them dimensioned to accommodate an adaptor 70 which will be described in detail later.

A nipple 162 is provided on the body 10 so as to cooperate with a hollow not shown and of which the location is referenced 62, under the cover 60 so as to arrest its possible translational movement by form interference when the cover is assembled on the body.

A description will now be given of a first example of use of this device.

Figure 2:
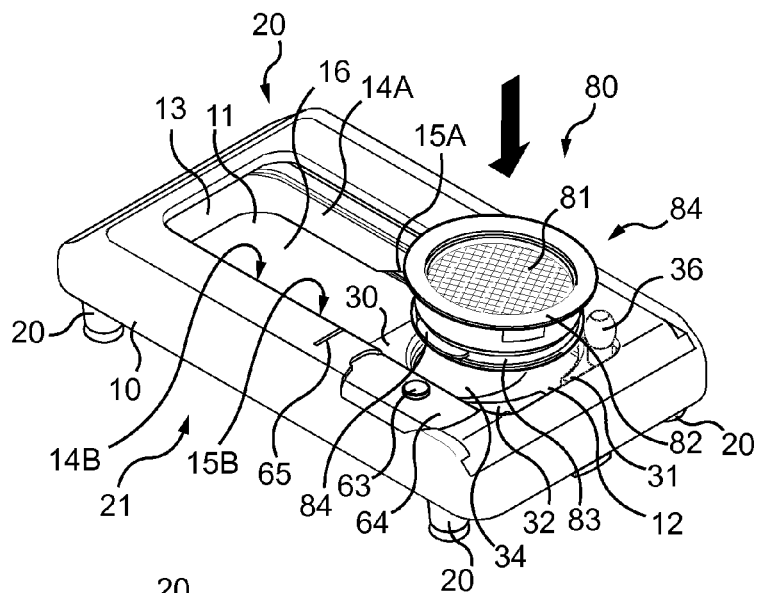
FIGS. 2 to 4 are perspective views of the same device represented in three consecutive steps of use with a first frame-and-support assembly.

As can be seen more particularly in FIG. 2, an assembly 80 is composed of a membrane 81 mounted in a frame 82, itself mounted on a support 83 containing a growth medium, here a solid gel support. In this example, the frame 83 comprises two diametrically opposite gripping member forming lugs 84 for the support.

The assembly 80 is inserted into the opening 34 of the shuttle 30 which is disposed at the first end 12 of the recess 11. The lugs 84 then come to be engaged in the recess 11 facing the ramps 15A and 15B.

The shuttle 30 thus clamped around the support forms bearing means for the frame during the translational movement between the first and the second end of the recess.

To separate the membrane 81 from the support 83, the operator performs the translational movement of the shuttle 30 towards the second end 13 of the opening 11 using the handle 36. During this translational movement, the stud 35 passes across the cam of the channel 17, the effect of which is to bring towards each other the two halves 31 and 32 of the shuttle which then slides along the rods 33, and thus to clamp around the frame 82. At the same time, the nipples 38 pass across the cam tracks of the grooves 18A and 18B to accompany the movement of clamping around the frame from the four corners of the shuttle. In parallel with this, the lugs 84 engage the ramps 15A and 15B so as to separate the frame from the support during the action of translational movement.

Once the frame has been separated from the support, the latter is guided towards the hole 16 of the recess 11 to fall into the space 21 situated under the body 10.

When, in its translational movement, the shuttle reaches the end of its travel at the second end 13 of the recess 11, the end of the stud 35 engages the cam forming portion of the groove 52 of the lever 50, so forcing it to pivot around the pivot 51. The lever 50 then comes to push the support 83 out from the space 21, which facilitates its retrieval by the manipulator.

The shuttle is then again translationally moved towards the first end 12 of the recess 11, the effect of which is to return the lever 50 into its initial position and to open the two halves 31 and 32 of the shuttle 30 so permitting the operator to extract the frame bearing the membrane which is now separated from its support.

Figure 3:
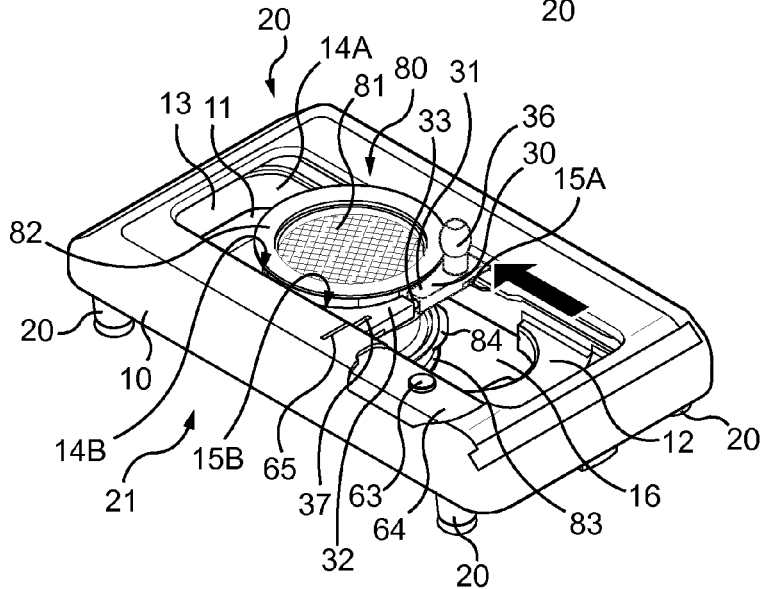

It will be noted in FIGS. 1 and 3, that a mark 65 is provided on the cover 60 and that a mark 37 is provided on the shuttle 30. These two marks are situated facing each other in FIG. 3 to visually indicate to the operator that the lever 50 is on the point of ejecting the support. This marker enables the operator to slow the translational movement as from that particular moment, to avoid an ejection that is too fast and far from the support.

Figure 5:
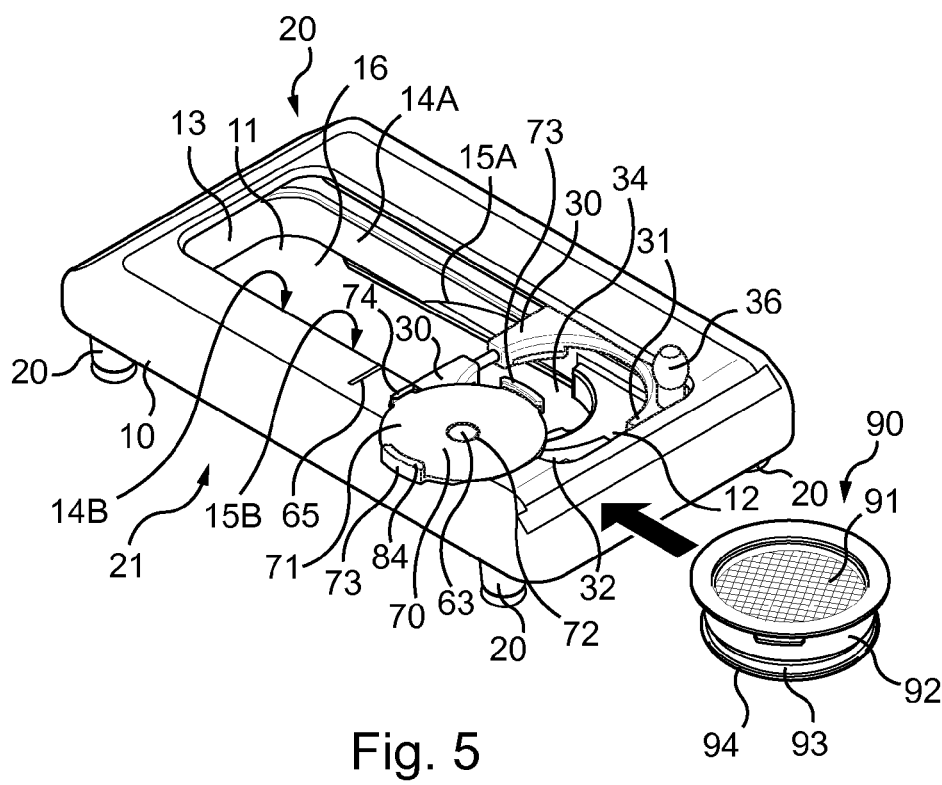
FIGS. 5 to 7 are perspective views of the same device representing the successive steps of its use with another frame-and-support assembly combined with an adaptor.
Figure 6:
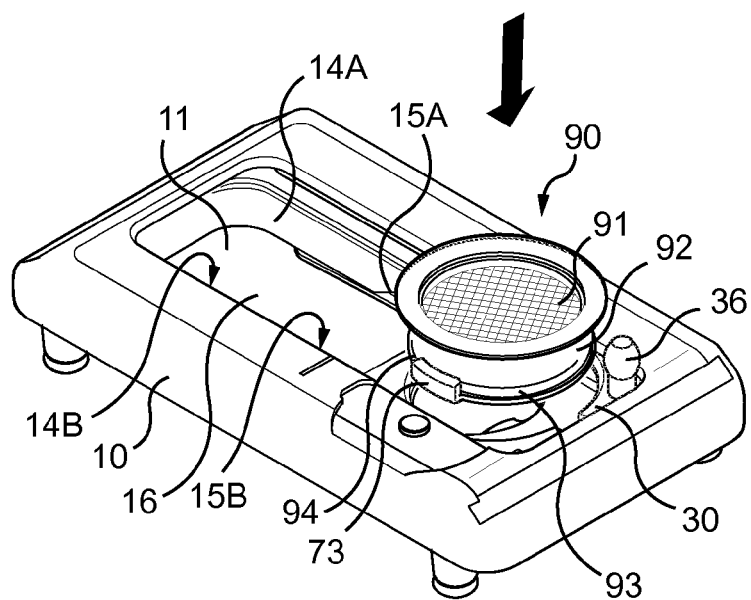
Figure 7:
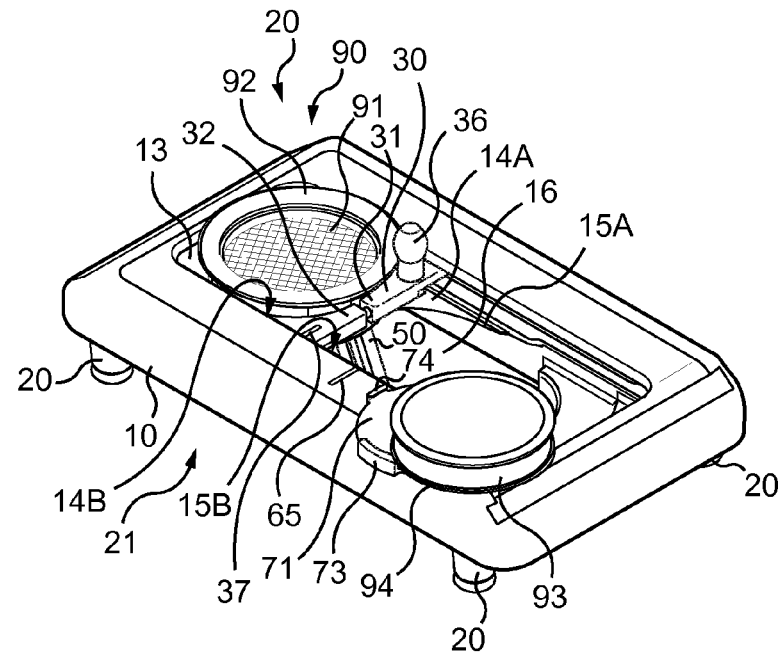

A description will now be given of another embodiment of the same device, this time with a frame-and-support assembly not comprising any gripping means forming lug. This example is illustrated in FIGS. 5 to 7. As the device is the same, the reference numbers are kept the same. Only the reference numbers of the frame-and-support assembly have been changed.

As can be seen in FIG. 5, an assembly 90 composed of a membrane 91 mounted in a frame 92 itself mounted on a support 93 containing a medium, here a pad impregnated with a liquid growth medium or a marking medium, is presented in front of the device 1 for the purpose of separating the membrane from the support. The support 93 has a flat 94 on its periphery.

To mitigate the lack of any lug serving as gripping member for the support, an adaptor 70 has been provided. The adaptor 70 comprises a plate 71 pierced by a hole 72 dimensioned so as to cooperate with the nipple 63 provided for that purpose on the cover 60, on respective opposite sides of the plate 71, two hooks 73 are located diametrically opposite and are dimensioned so as to engage in the flat 94 of the support by translational movement. A stop 74 is provided half way between the hooks 73 to facilitate the centering of the assembly 90 on the adaptor 70. Thus, the adaptor transfers the gripping zone of the support from the flat 94 to the hooks 73, so adapting the support 93 to the device described above. The stop 74 has the form of a hook to improve its attachment.

Figure 4:
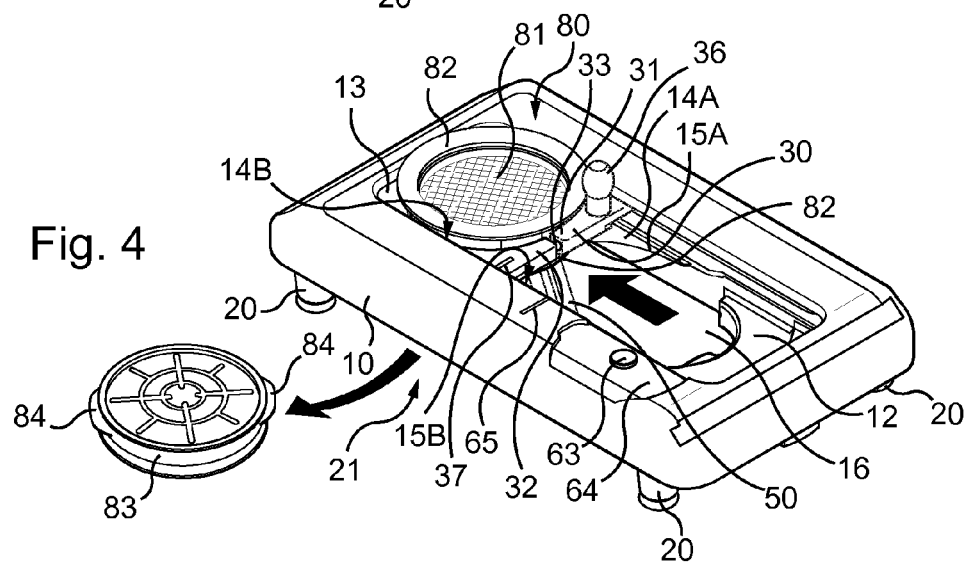

To that end, the adaptor 70 is placed on the nipple 63 in the recess 64 so as to make it easier for the operator to insert the assembly 90 into the hooks 73 until the stop 74 is reached. Once this insertion has been carried out, the operator introduces the assembly 90 completed by the adaptor 70 into the opening 34 of the shuttle 30. The hooks 73 then form a gripping member of the support for the device and the separation of the membrane and of the support is continued in a strictly similar way to that which can be seen in FIGS. 3 and 4.

Through an advantageous effect, the stop 74 avoids the support 93 slipping out of the adaptor during the separation.

Once the support 93 has been extracted from the device, as can be seen in FIG. 7, the adaptor 70 is re-positioned on the stud 63 and the support is extracted by a translational movement so as to retrieve the adaptor 70.

The frame 91 bearing the membrane may then be retrieved from the device in similar manner to that described in the preceding example.

Figure 8:
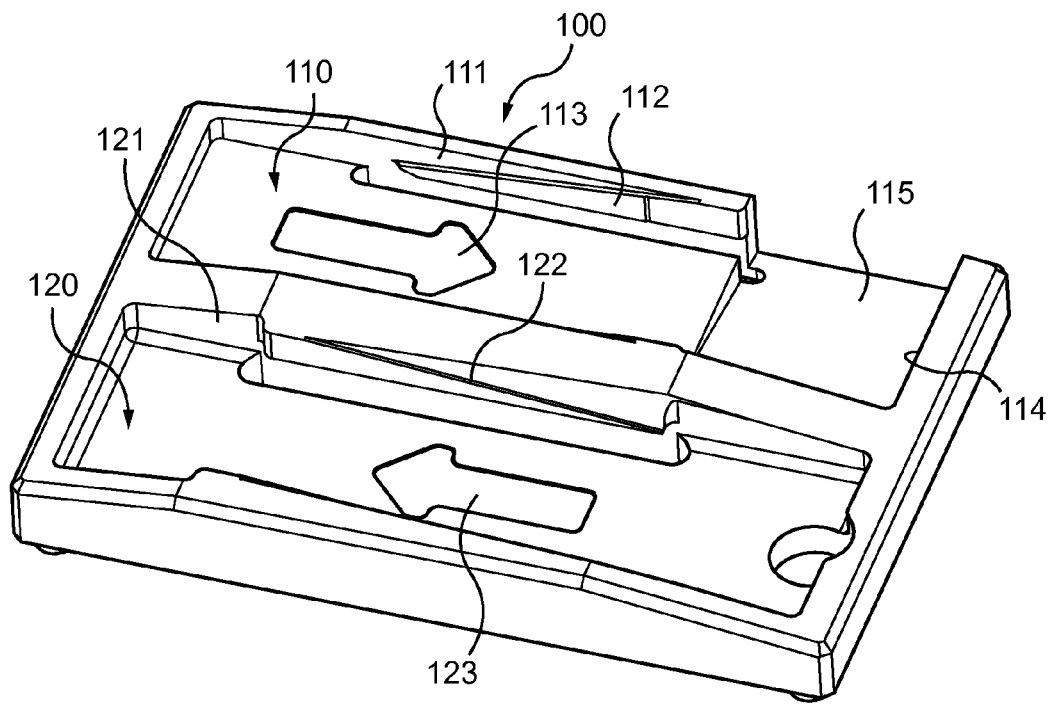
FIG. 8 is a view of another embodiment of a device according to the invention.

Another embodiment of a device according to the invention can be seen in FIG. 8.

This separation device 100 comprises two longitudinal recesses 110 and 120, each adapted to a different type of support-and-frame assembly.

In similar manner to that described for the preceding examples, each of the recesses comprises two longitudinal sides 111 and 121 each comprising ramps 112 and 122 which are symmetrical in each recess and which are adapted to separate the support from the frame.

In this embodiment, the ramps in reality have the shape of wedges each having a lower face and an upper face which move apart from each other in the directions of translational movement diagrammatically represented by the arrows 113 and 123 respectively for the recesses 110 and 120.

These ramps are adapted to engage between a bearing surface of a first member of the frame/support group and a gripping member of the second member of the frame/support group (not shown) so as to separate the frame from the support during the translational movement in each of the recesses.

Lastly it will be noted that the recess 110 comprises at a second end 114 an inclined plane 115 provided for ejecting the support once this has been separated from the frame which is then still substantially bearing on the ramps 112.

Naturally, many modifications can be made to the embodiment described above without departing from the scope of the invention.

The invention claimed is:

1. A device for separating a membrane to analyze from a support, the membrane being mounted in a frame, itself mounted on the support, said device comprising a body comprising a longitudinal recess for translational reception of the frame mounted on the support, the recess having a first end and a second end and longitudinal sides facing each other between said two ends, the device further comprising a shuttle for a first member of the frame and support between the first and the second end of the recess, which is adapted to serve as a bearing for the first member of the frame and support once the frame and support is disposed in the recess, each of the sides having a ramp adapted to engage a gripping member of a second member of the frame and support when the frame and support is translationally moved from the first to the second end, said ramps being adapted to separate the support from the frame during said translational movement by bearing on said gripping member of the second member of the frame and support, the first member of the frame and support then bearing on the shuttle, such that the frame and the support are separated once the translational movement has arrived at the second end.

2. A device according to claim 1, wherein the body has foot forming means adapted to form a space between the body and a surface on which the device is placed, the recess having, at least at its second end, a hole opening towards said space and the ramps have a profile adapted to guide the support towards said hole to eject the support from the device via the hole towards said space once the separation has been carried out and the translational movement has arrived at said second end.

3. A device according to claim 2, wherein said shuttle is mounted for translational movement in the recess between said first and said second end, the shuttle having an opening adapted to accommodate the frame and support during the translational movement.

4. A device according to claim 3, wherein the shuttle has clamping means actuated by a cam action cooperating with the body of the device and which are adapted to clamp the frame once the shuttle has left the first end.

5. A device according to claim 3, further comprising an ejecting lever rotatably mounted relative to the body in said space, and which is adapted to be pivoted by cam action on movement of the shuttle from the first to the second end so as to make the support come out of said space once the ejection has been performed via the hole.

6. A device according to claim 1, further comprising an adaptor provided for engaging with a flat provided on the support and for forming gripping means for the separation ramps.

7. A device according to claim 6, wherein it has fastening means for the adaptor provided for retaining the adaptor in a position in which the support is assembled with the adaptor before the frame and support is placed in the recess.

8. A device according to claim 1, further comprising a plurality of recesses provided with corresponding ramps, which recesses are each adapted to cooperate with a different predefined frame and support.

9. A method of separating a membrane to analyze from a support, the membrane being mounted in a frame, itself mounted on the support using a device according to claim 1, comprising:

providing the device of claim 1, placing the frame and the support in the recess at its first end, causing the frame and support to move translationally from the first to the second end of the recess to separate the support from the frame, removing the separated frame from the device.

10. A method of separating a membrane to analyze from a support, the membrane being mounted in a frame, itself mounted on the support using a device according to claim 6, comprising:

providing the device of claim 6, assembling the support with the adaptor, placing the frame and the support with the adaptor in the recess at its first end, causing the frame and support to move translationally from the first to the second end of the recess to separate the support from the frame, removing the separated frame from the device, removing the support from the adaptor.

* * * * *